United States Patent
Inoue

(10) Patent No.: US 10,930,030 B2
(45) Date of Patent: Feb. 23, 2021

(54) IMAGE PROCESSING APPARATUS, IMAGE PROCESSING METHOD, AND PROGRAM

(71) Applicant: CANON KABUSHIKI KAISHA, Tokyo (JP)

(72) Inventor: Noboru Inoue, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 90 days.

(21) Appl. No.: 16/428,808

(22) Filed: May 31, 2019

(65) Prior Publication Data
US 2019/0371015 A1 Dec. 5, 2019

(30) Foreign Application Priority Data

Jun. 4, 2018 (JP) .............................. JP2018-106942

(51) Int. Cl.
| G06T 11/00 | (2006.01) |
| G06T 7/00 | (2017.01) |
| G06T 7/73 | (2017.01) |
| G06K 9/00 | (2006.01) |
| G16H 30/40 | (2018.01) |

(52) U.S. Cl.
CPC ........ *G06T 11/005* (2013.01); *G06K 9/00369* (2013.01); *G06T 7/0014* (2013.01); *G06T 7/74* (2017.01); *G16H 30/40* (2018.01); *G06T 2207/10116* (2013.01); *G06T 2207/20221* (2013.01); *G06T 2207/30004* (2013.01)

(58) Field of Classification Search
CPC ....... G06T 11/005; G06T 7/74; G06T 7/0014; G06T 2207/10116; G06T 2207/20221; G06T 2207/30004; G16H 30/40; G06K 9/00369

See application file for complete search history.

(56) References Cited

U.S. PATENT DOCUMENTS

| 9,508,127 B1* | 11/2016 | Katsuhara | ............... G06T 5/002 |
| 10,219,770 B2* | 3/2019 | Enomoto | ............... A61B 6/463 |
| 10,342,508 B2* | 7/2019 | Matsushita | ............ A61B 6/545 |
| 2010/0014780 A1* | 1/2010 | Kalayeh | .................. G06T 5/002 382/284 |
| 2011/0033101 A1* | 2/2011 | Foos | ..................... A61B 6/5252 382/132 |
| 2013/0114790 A1* | 5/2013 | Fabrizio | ................... A61B 6/02 378/62 |
| 2014/0119500 A1* | 5/2014 | Akahori | ................. A61B 6/585 378/17 |
| 2015/0247936 A1* | 9/2015 | Gemma | ................ G01T 1/2012 250/363.01 |

(Continued)

FOREIGN PATENT DOCUMENTS

JP          2012-040140 A          3/2012

*Primary Examiner* — Utpal D Shah
(74) *Attorney, Agent, or Firm* — Canon U.S.A., Inc. IP Division

(57) ABSTRACT

An image processing apparatus according to an example embodiment includes a storage unit configured to store a relative position and an angle of each of a plurality of radiation detection apparatuses attached to a platform in first imaging and a composition unit configured to, on the basis of the relative position and angle of each of the radiation detection apparatuses which are stored in the storage unit, combine a plurality of images obtained by a plurality of radiation detection apparatuses in second imaging subsequent to the first imaging.

20 Claims, 5 Drawing Sheets

(56) References Cited

U.S. PATENT DOCUMENTS

| | | | |
|---|---|---|---|
| 2015/0251018 A1* | 9/2015 | Tajima | A61B 6/4233 |
| | | | 378/28 |
| 2016/0220213 A1* | 8/2016 | Miyamoto | A61B 6/5258 |
| 2016/0296189 A1* | 10/2016 | Suzuki | A61B 6/5205 |
| 2019/0029627 A1* | 1/2019 | Katsushima | A61B 6/4266 |
| 2019/0046130 A1* | 2/2019 | Imamura | A61B 6/4283 |
| 2019/0223820 A1* | 7/2019 | Nemoto | G06T 5/20 |

* cited by examiner

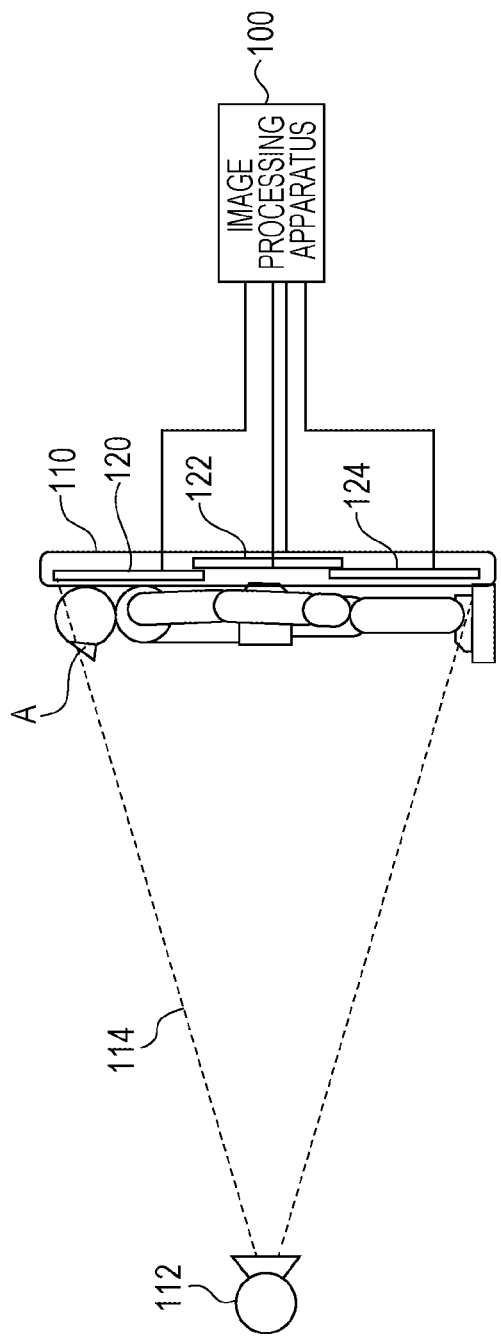

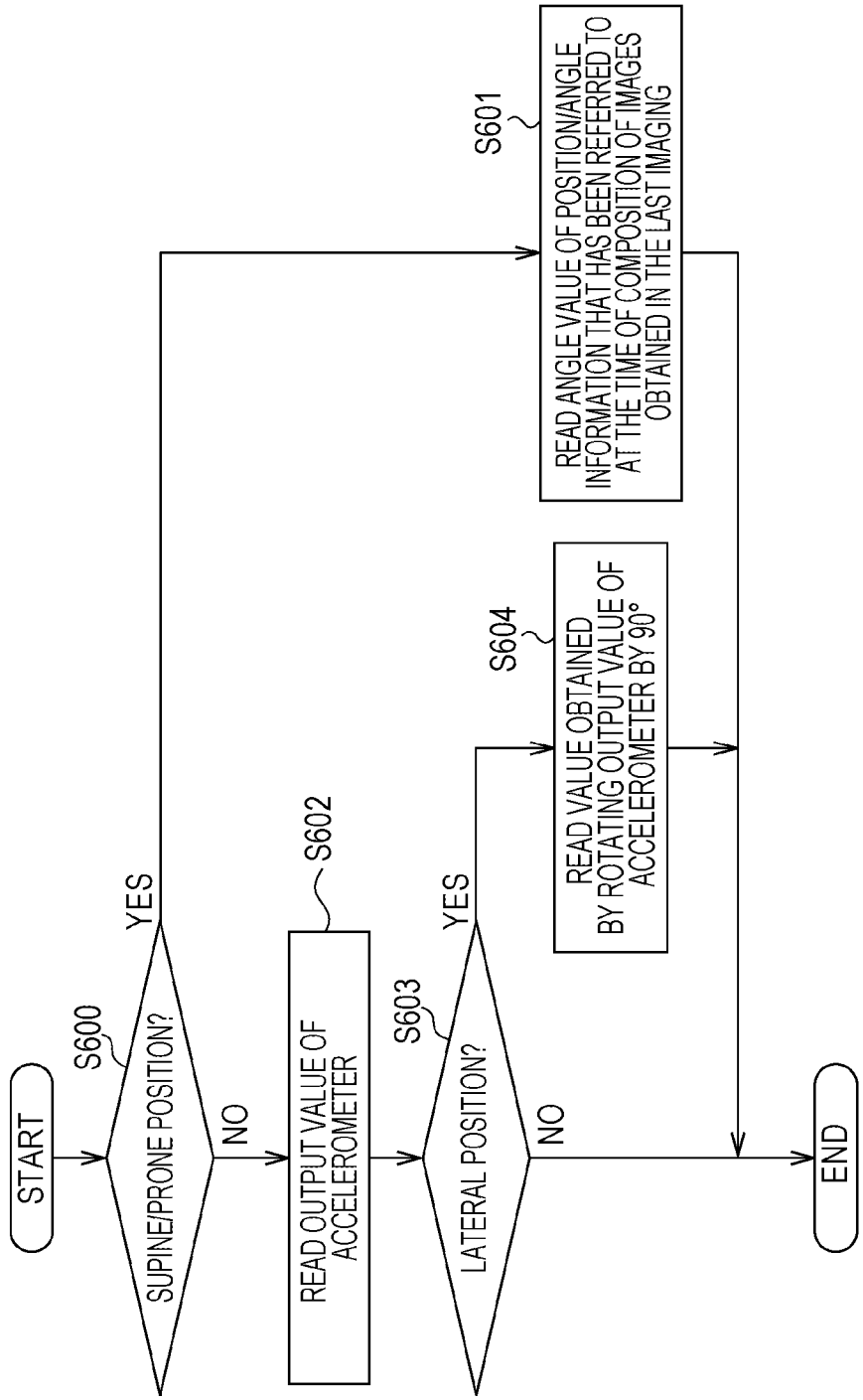

IMAGE PROCESSING APPARATUS, IMAGE PROCESSING METHOD, AND PROGRAM

BACKGROUND

Field

The present disclosure relates to an image processing apparatus for processing radiographic images, an image processing method of processing radiographic images, and a program.

Description of the Related Art

In the medical field, the imaging of the entirety of the spine, lower limb, or body of a subject has been performed. Such imaging is performed upon a wide observation area (hereinafter referred to as "long-length imaging"). Japanese Patent Laid-Open No. 2012-040140 discloses a radiographic imaging system capable of performing long-length imaging using a plurality of arranged radiation detection apparatuses (radiographic imaging apparatuses). In this radiographic imaging system, portable radiation detection apparatuses are used. The radiation detection apparatuses disposed on a dedicated platform are used to perform long-length imaging, and only one of them can be separated from the platform to perform general imaging.

In such use of radiation detectors, when the arrangement sequence and orientations of the radiation detectors at the time of long-length imaging change, the arrangement sequence and orientations of images output by the respective radiation detectors change. For example, an operator can solve this problem by being careful not to change the arrangement sequence of the radiation detectors or by being aware that the arrangement sequence and orientations of the radiation detectors have changed and rotating and rearranging the radiation detectors in a radiographic imaging system. However, the workload of the operator increases.

SUMMARY

Some embodiments provide an image processing apparatus and an image processing method which can combine appropriate long-length images without increasing the workload of an operator.

An image processing apparatus according to an embodiment of the present disclosure includes a storage unit configured to store a relative position and an angle of each of a plurality of radiation detection apparatuses attached to a platform in first imaging and a composition unit configured to, on the basis of the relative position and angle of each of the radiation detection apparatuses which are stored in the storage unit, combine a plurality of images obtained by a plurality of radiation detection apparatuses in second imaging subsequent to the first imaging.

Further features of various embodiments will become apparent from the following description of exemplary embodiments with reference to the attached drawings.

BRIEF DESCRIPTION OF THE DRAWINGS

FIG. 1 is an overall view of a radiographic imaging system.

FIG. 6 is a flowchart illustrating an embodiment of an angle setting process.

DESCRIPTION OF THE EMBODIMENTS

Some embodiments will be described below with reference to the accompanying drawings.

First Embodiment

FIG. 1 is an overall view of a radiographic imaging system according to the first embodiment. The radiographic imaging system includes a radiation generation unit 112 for generating radiation. The radiation generation unit 112 can emit radiation in an irradiation range 114. The radiation generation unit 112 is disposed via a supporting unit (not illustrated) provided on a floor or a ceiling. A diaphragm (not illustrated) for shielding radiation is disposed on an irradiation face of the radiation generation unit 112. An operator can set the irradiation range 114 of radiation emitted from the radiation generation unit 112 by controlling the diaphragm for shielding radiation.

The radiographic imaging system includes a plurality of radiation detection apparatuses 120, 122, and 124. The number of radiation detection apparatuses included in the radiographic imaging system may be greater than or equal to 2, and is not limited to the number described in an embodiment. Each of the radiation detection apparatuses 120, 122, and 124 detects radiation passing through a subject A and outputs image data based on the radiation. The image data can also be referred to as a radiographic image. Each of the radiation detection apparatuses 120, 122, and 124 detects radiation passing through a subject as electric charges corresponding to the amount of penetrating radiation. Examples of the radiation detection apparatuses 120, 122, and 124 include a direct conversion sensor using amorphous selenium (a-Se) which directly converts radiation into electric charges or an indirect sensor using a scintillator containing cesium iodide (CsI) and a photoelectric conversion element containing amorphous silicon (a-Si). Each of the radiation detection apparatuses 120, 122, and 124 generates image data by performing analog-to-digital (A/D) conversion upon detected electric charges and outputs the generated image data to an image processing apparatus 100.

The radiation detection apparatuses 120, 122, and 124 are set in an imaging table 110. The imaging table 110 is a rectangular housing, and, more specifically, a hollow long-length platform. The imaging table 110 has a function of holding the radiation detection apparatuses 120, 122, and 124. As illustrated in FIG. 1, the imaging table 110 is disposed in an upright position with respect to the floor. The subject A is placed along the lengthwise direction of the imaging table 110. The imaging table 110 has a function of supporting the subject A.

Figure 2A:
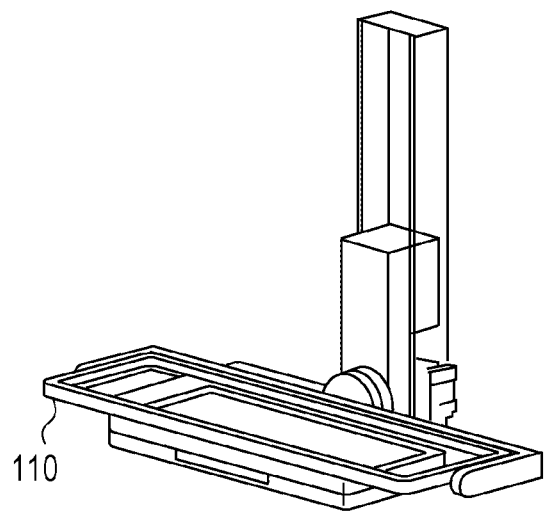
FIGS. 2A and 2B are diagrams describing the direction of an imaging table.
Figure 2B:
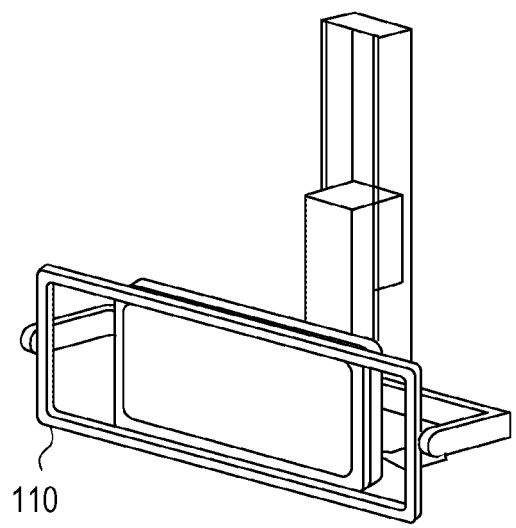

In FIG. 1, the imaging table 110 is disposed such that the lengthwise direction of the imaging table 110 is in a vertical direction, that is, the imaging table 110 is in an upright position with respect to the floor. This disposition direction is hereinafter referred to as an erect position. As illustrated in FIG. 2A, the imaging table 110 may be disposed such that the lengthwise direction of the imaging table 110 is in a horizontal direction, that is, the imaging table 110 is parallel to the floor. This disposition direction is hereinafter referred to as a supine/prone position. As illustrated in FIG. 2B, the imaging table 110 may be disposed such that the lengthwise direction of the imaging table 110 is in the horizontal direction and the transverse direction of the imaging table 110 is in the vertical direction. This disposition direction is hereinafter referred to as a lateral position.

In the imaging table 110, the radiation detection apparatuses 120, 122, and 124 are arranged in the lengthwise direction of the imaging table 110. The radiation detection apparatuses 120, 122, and 124 are disposed to partly overlap each other. For example, as illustrated in FIG. 1, the radiation detection apparatuses 120 and 122 are disposed such that parts of them spatially overlap each other. In this case, the imageable regions of the radiation detection apparatuses 120 and 122 overlap each other. Similarly, the radiation detection apparatuses 122 and 124 are disposed such that parts of them spatially overlap each other. In this case, the imageable regions of the radiation detection apparatuses 122 and 124 overlap each other. The radiation detection apparatus 122 is disposed on the backside of the radiation detection apparatuses 120 and 124, that is, at a position farther from the radiation generation unit 112 than the radiation detection apparatuses 120 and 124. In another example, the radiation detection apparatus 120 may be disposed on the backside of the radiation detection apparatus 122 and the radiation detection apparatus 122 may be disposed on the backside of the radiation detection apparatus 124.

The radiographic imaging system includes the image processing apparatus 100 for performing image processing upon image data output from the radiation detection apparatus to generate an image. The image processing apparatus 100, the radiation detection apparatuses 120, 122, and 124, and the imaging table 110 are connected to one another via a wired or wireless network or a dedicated line. Each of the radiation detection apparatuses 120, 122, and 124 performs the imaging of radiation generated by the radiation generation unit 112 and outputs image data to the image processing apparatus 100. The image processing apparatus 100 has an application function operating on a computer. The image processing apparatus 100 controls the operations of the radiation detection apparatuses 120, 122, and 124.

The image processing apparatus 100 controls the radiation generation timing and radiation imaging conditions of the radiation generation unit 112. The image processing apparatus 100 controls the image data acquisition timing and image data output timing of each of the radiation detection apparatuses 120, 122, and 124. The image processing apparatus 100 can cause the radiation detection apparatuses 120, 122, and 124 to perform imaging at the same time and output image data at the same time. The image processing apparatus 100 can perform image processing, such as noise reduction, trimming, or rotating, upon image data output from each of the radiation detection apparatuses 120, 122, and 124.

The subject A stands on a step placed at the imaging table 110, so that the position thereof is fixed with respect to the radiation detection apparatuses 120, 122, and 124 and the radiation generation unit 112. In this embodiment, the imaging table 110 is disposed such that radiation vertically enters the center of the radiation detection apparatus 122. Radiation emitted from the radiation generation unit 112 to the radiation detection apparatuses 120, 122, and 124 passes through the subject A, reaches the radiation detection apparatuses 120, 122, and 124, and is detected. The image processing apparatus 100 combines pieces of image data acquired by the radiation detection apparatuses 120, 122, and 124 to generate the combined image of the subject A. The combined image is a long-length image acquired by long-length imaging performed upon a wide observation area. The image processing apparatus 100 displays the long-length image.

Figure 3:
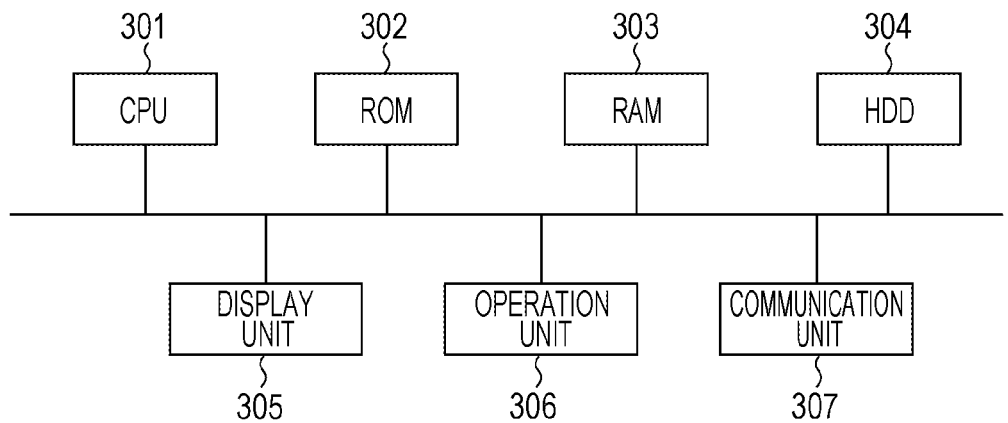
FIG. 3 is a diagram illustrating the hardware configuration of an embodiment of an image processing apparatus.

FIG. 3 is a diagram illustrating the hardware configuration of an embodiment of the image processing apparatus 100. The image processing apparatus 100 includes a central processing unit (CPU) 301, a read-only memory (ROM) 302, a random access memory (RAM) 303, a hard disk drive (HDD) 304, a display unit 305, an operation unit 306, and a communication unit 307. The CPU 301 reads a control program stored in the ROM 302 to perform various pieces of processing. The RAM 303 is used as a main memory and a temporary storage area such as a work area for the CPU 301. The HDD 304 stores various pieces of data and various programs. The display unit 305 displays various pieces of information. The operation unit 306 includes a keyboard and a mouse to accept various operations performed by a user. The communication unit 307 communicates with an external apparatus via a network.

The functions and processing of the image processing apparatus 100 to be described below are realized by causing the CPU 301 to read programs stored in the ROM 302 or the HDD 304 and execute the read programs. In another example, the CPU 301 may read programs that are not stored in, for example, the ROM 302 but in, for example, an SD card.

In another example, at least parts of the functions and processing of the image processing apparatus 100 may be realized by causing, for example, a plurality of CPUs, a RAM, a ROM, and a storage to corporate with one another. In still another example, at least parts of the functions and processing of the image processing apparatus 100 may be realized using a hardware circuit.

Figure 4:
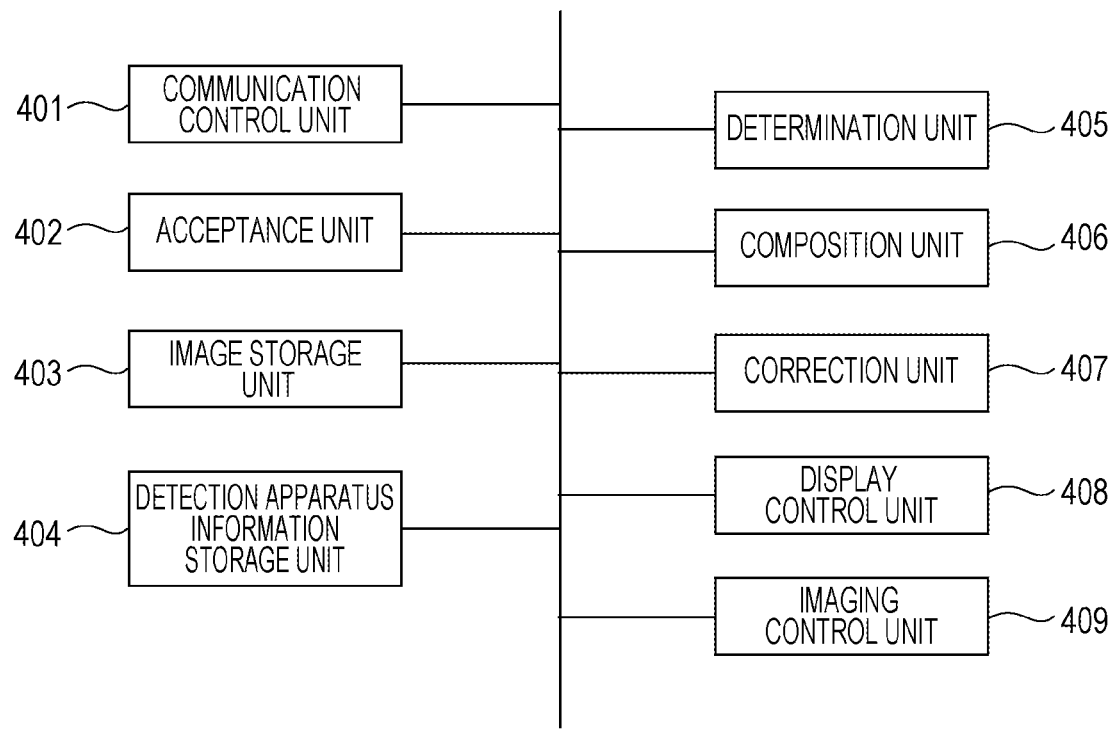
FIG. 4 is a diagram illustrating the functional configuration of an embodiment of an image processing apparatus.

FIG. 4 is a diagram illustrating the functional configuration of the image processing apparatus 100. The image processing apparatus 100 includes a communication control unit 401, an acceptance unit 402, an image storage unit 403, a detection apparatus information storage unit 404, a determination unit 405, a composition unit 406, a correction unit 407, a display control unit 408, and an imaging control unit 409. The communication control unit 401 controls communication with an external apparatus. The acceptance unit 402 accepts information input via the operation unit 306. The image storage unit 403 stores image data output from each of the radiation detection apparatuses 120, 122, and 124 along with time information.

The detection apparatus information storage unit 404 associates the identification information of each of the radiation detection apparatuses 120, 122, and 124 and position/angle information with each other and stores them. The position/angle information is information about the relative position and angle (orientation) of each of the radiation detection apparatuses 120, 122, and 124 with respect to the imaging table 110. When an operator inputs the position/angle information of each of the radiation detection apparatuses 120, 122, and 124 via the operation unit 306, the acceptance unit 402 accepts the input operation and stores the position/angle information in the detection apparatus information storage unit 404. This processing is an example of management processing. The imaging table 110 includes a detection unit for detecting the relative position/angle and identification information of an attached apparatus (each of the radiation detection apparatuses 120, 122, and 124) in the imaging table 110. The communication control unit 401 receives the position/angle information representing the position and angle of a radiation detection apparatus and the identification information from the imaging table 110 and stores them in the detection apparatus information storage unit 404. In the initial state of the detection apparatus information storage unit 404, the initial values of a position and an angle are set as the position/angle information. More specifically, as the initial values, values are set which are obtained in a state where the radiation detection apparatuses 120, 122, and 124 are disposed in this order from the top of the imaging table 110 and the disposition orientation of each apparatus is 0°. However, the initial values may be optionally set and are not limited to the values in an embodiment.

The determination unit 405 determines whether it can refer to the arrangement of the radiation detection apparatuses 120, 122, and 124 which has been referred to at the time of the last composition of images. This processing will be described below. The composition unit 406 combines three images acquired from the respective radiation detection apparatuses 120, 122, and 124 to acquire a long-length image. For example, in the example illustrated in FIG. 1, image data output from the radiation detection apparatus 120 is positioned on the upper side, image data output from the radiation detection apparatus 124 is positioned on the lower side, and image data output from the radiation detection apparatus 122 is positioned therebetween. The composition unit 406 combines a plurality of images on the basis of these pieces of positional information and the orientations of the radiation detection apparatuses to acquire a long-length image. The correction unit 407 performs correction, such as noise reduction, upon the long-length image. The display control unit 408 performs control processing to display the corrected long-length image on the display unit 305. The imaging control unit 409 controls radiographic imaging.

Figure 5:
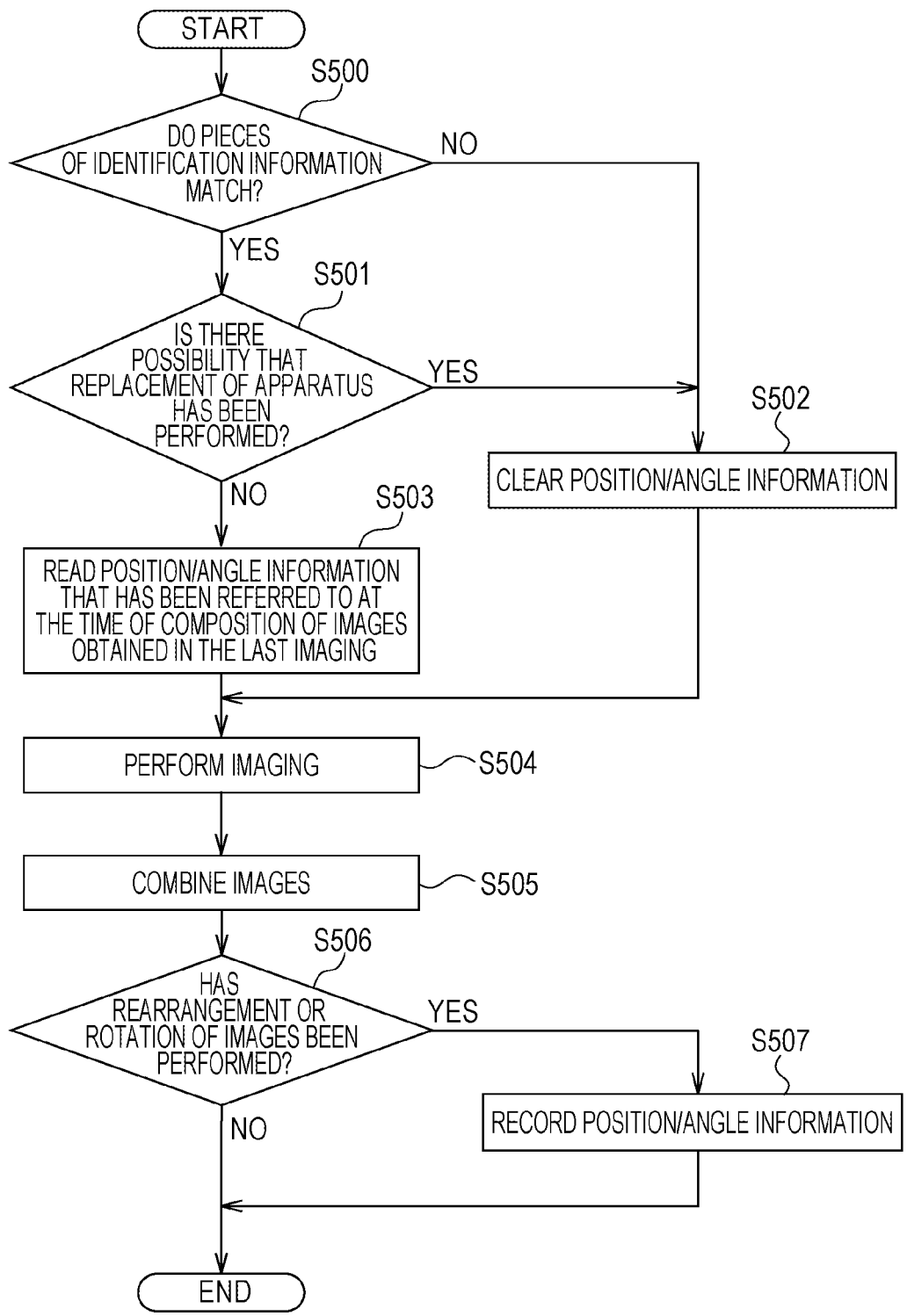
FIG. 5 is a flowchart illustrating an embodiment of an image processing process.

FIG. 5 is a flowchart illustrating an embodiment of an image processing process performed by the image processing apparatus 100. In S500, the communication control unit 401 acquires the identification information of an apparatus attached to the imaging table 110 at the time of the image processing process. In another example, the identification information of an apparatus attached to the imaging table 110 at the time of the image processing process may be input through a user's operation. In this case, the acceptance unit 402 receives the identification information. The determination unit 405 determines whether the identification information of the apparatus attached to the imaging table 110 and identification information stored in the detection apparatus information storage unit 404 match each other. In this embodiment, it is determined whether all of the three pieces of information of the three apparatuses attached to the imaging table 110 match corresponding stored pieces of identification information. In a case where the three pieces of identification information match the corresponding stored pieces of identification information (YES in S500), the process proceeds to S501. In a case where there is a piece of identification information that does not match corresponding stored identification information (NO in S500), the process proceeds to S502.

In S501, it is determined whether there is a possibility that the replacement of an apparatus has been performed. In a case where at least two apparatuses are removed, a possibility arises where the changes in the positions of the apparatuses may occur. Accordingly, in a case where two apparatuses have been removed, the determination unit 405 determines that there is a possibility that the replacement of an apparatus has been performed. The imaging table 110 includes an apparatus attachment/detachment sensor. The communication control unit 401 can determine whether an apparatus has been removed by receiving a detection result of the apparatus attachment/detachment sensor from the imaging table 110. In a case where there is a possibility that the replacement of an apparatus has been performed (YES in S501), the process proceeds to S502. In a case where there is not a possibility that the replacement of an apparatus has been performed (NO in S501), the process proceeds to S503.

In S502, the determination unit 405 clears the position/angle information stored in the detection apparatus information storage unit 404. That is, the determination unit 405 sets the value of the position/angle information back to the initial value. Subsequently, the process proceeds to S504.

In S503, the determination unit 405 reads from the detection apparatus information storage unit 404 the position/angle information that has been referred to at the time of composition of images obtained in the last radiographic imaging, that is, the position/angle information stored in the detection apparatus information storage unit 404. Subsequently, the process proceeds to S504. In S504, the imaging control unit 409 performs control processing such that radiographic imaging is performed.

Subsequently, in S505, the composition unit 406 performs image rotation and image rearrangement upon three images as appropriate on the basis of the position/angle information read in S503 at the time of combining the three images to acquire a long-length image. The display control unit 408 displays the acquired long-length image on the display unit 305. An operator visually checks the long-length image displayed on the display unit 305. In a case where the operator finds an image orientation error or an image arrangement error, the operator performs a user's operation of correcting the error.

Subsequently, in a case where an instruction for at least one of image rotation and image rearrangement is made (YES in S506), the process proceeds to S507. In a case where neither of image rotation and image rearrangement is performed (NO in S506), the process ends. In S507, the determination unit 405 writes position/angle information obtained after the image rotation and the image rearrangement over the position/angle information stored in the detection apparatus information storage unit 404. The process ends.

As described above, the image processing apparatus 100 according to this embodiment uses the position/angle information, which has been used for images obtained in the first imaging, when combining images obtained in the second imaging subsequent to the first imaging. An operator therefore does not need to set the position and orientation of each radiation detection apparatus. Accordingly, the image processing apparatus 100 can combine appropriate long-length images without increasing the workload of an operator.

Second Embodiment

Next, the different point of a radiographic imaging system according to the second embodiment from a radiographic imaging system according to the first embodiment will be mainly described. In the second embodiment, each of the radiation detection apparatuses 120, 122, and 124 includes an accelerometer. FIG. 6 is a flowchart illustrating an angle setting process performed by the image processing apparatus 100 according to the second embodiment. The angle setting process is performed in S503 described with reference to FIG. 5. In the second embodiment, the image processing apparatus 100 acquires positional information by reading the value of the position/angle information and acquires angle information by reading the value in this angle setting process.

In S600, the determination unit 405 determines the disposition direction of the imaging table 110. In a case where the disposition direction is the supine/prone position (YES in S600), the process proceeds to S601. In a case where the disposition direction is not the supine/prone position (NO in S600), the process proceeds to S602. In S601, the determination unit 405 reads the angle value of the position/angle information that has been referred to at the time of composition of images obtained in the last imaging. The process ends. In the case of the supine/prone position, it is impossible to determine which direction the radiation detection apparatus is disposed with respect to the imaging table 110 on the basis of the value of the accelerometer, because the imaging table 110 is disposed parallel to the floor. Accordingly, in the case of the supine/prone position, the angle value of the position/angle information that has been referred to at the time of composition of images obtained in the last imaging is read.

In S602, the determination unit 405 acquires the measurement result of each of the accelerometers in the radiation detection apparatuses 120, 122, and 124 via the communication control unit 401 and sets the measurement result as an angle. Subsequently, in S603, the determination unit 405 determines whether the disposition direction is the lateral position. In a case where the disposition direction is the lateral position (YES in S603), the process proceeds to S604. In a case where the disposition direction is not the lateral position (NO in S603), the process ends. In S604, the composition unit 406 reads, as an angle value, a value obtained by rotating the measurement result (output value) of the accelerometer in a direction opposite to the rotation direction of the imaging table 110 by 90°. The process ends. In the case of the erect position and the lateral position, the disposition direction of the radiation detection apparatus can be determined on the basis of the measurement result of the accelerometer. Accordingly, in the case of the erect position and the lateral position, the measurement result of the accelerometer is read as an angle value. The configuration and processing of a radiographic imaging system according to the second embodiment are the same as those of a radiographic imaging system according to the first embodiment.

According to the above-described embodiments, it is possible to combine appropriate long-length images without increasing the workload of an operator.

Other Embodiments

Some embodiment(s) can also be realized by a computer of a system or apparatus that reads out and executes computer-executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to various embodiments, it is possible to combine appropriate long-length images without increasing the workload of an operator.

While the present disclosure has described exemplary embodiments, it is to be understood that some embodiments are not limited to the disclosed exemplary embodiments. The scope of the following claims is to be accorded the broadest interpretation so as to encompass all such modifications and equivalent structures and functions.

This application claims priority to Japanese Patent Application No. 2018-106942, which was filed Jun. 4, 2018 and which is hereby incorporated by reference herein in its entirety.

What is claimed is:

1. An image processing apparatus comprising:
a storage unit configured to store a relative position and an angle of each of a plurality of radiation detection apparatuses attached to a long-length platform in first imaging; and
a composition unit configured to, on the basis of the relative position and angle of each of the radiation detection apparatuses which are stored in the storage unit, combine a plurality of images obtained by a plurality of radiation detection apparatuses in second imaging subsequent to the first imaging.

2. The image processing apparatus according to claim 1, further comprising a determination unit configured to determine whether the relative position and angle of each of the radiation detection apparatuses in the first imaging and a relative position and an angle of corresponding one of the radiation detection apparatuses in the second imaging match each other,
wherein, on the basis of a determination result of the determination unit, the composition unit combines the images obtained by the radiation detection apparatuses in the second imaging.

3. The image processing apparatus according to claim 1, wherein the storage unit stores identification information of each of the radiation detection apparatuses in the first imaging along with the relative position and the angle, and
wherein, in a case where identification information of each radiation detection apparatus used in the second imaging and the corresponding identification information stored in the storage unit match each other, the composition unit combine a plurality of images on the basis of the relative position and angle of each of the radiation detection apparatuses in the first imaging.

4. The image processing apparatus according to claim 3, further comprising a management unit configured to, in a case where identification information of each radiation detection apparatus used in the second imaging and the corresponding identification information stored in the storage unit do not match each other, change the corresponding relative position and the corresponding angle stored in the storage unit to initial values set in advance.

5. The image processing apparatus according to claim 1, further comprising:
a first acceptance unit configured to receive at least one of an instruction for rearrangement of the images and an instruction for rotation of the images; and
a management unit configured to change at least one of the relative position and the angle stored in the storage unit in response to the instruction.

6. The image processing apparatus according to claim 1, further comprising:
a second acceptance unit configured to receive a relative position and an angle of each of the radiation detection apparatuses; and
a management unit configured to store the relative position and the angle received by the second acceptance unit in the storage unit.

7. The image processing apparatus according to claim 1, wherein, in a case where a disposition direction of the long-length platform is a supine/prone position, the composition unit refers to the angle stored in the storage unit.

8. The image processing apparatus according to claim 7, wherein, in a case where a disposition direction of the long-length platform is an erect position or a lateral position, the composition unit refers to a measurement result of an accelerometer disposed at each of the radiation detection apparatuses instead of the angle stored in the storage unit.

9. An image processing method performed by an image processing apparatus, the method comprising:
combining, on the basis of a relative position and an angle of each of radiation detection apparatuses attached to a long-length platform in first imaging which are stored in a storage unit, a plurality of images obtained by the radiation detection apparatuses.

10. The image processing method according to claim 9, further comprising determining whether the relative position and angle of each of the radiation detection apparatuses in first imaging and a relative position and an angle of corresponding one of radiation detection apparatuses in second imaging match each other,
wherein, on the basis of a determination result in the determining, a plurality of images obtained by the radiation detection apparatuses in the second imaging are combined in the combining.

11. The image processing method according to claim 9, wherein the storage unit stores identification information of each of the radiation detection apparatuses in the first imaging along with the relative position and the angle, and
wherein, in a case where identification information of each radiation detection apparatus used in the second imaging and the corresponding identification information stored in the storage unit match each other, a plurality of images are combined in the combining on the basis of the relative position and angle of each of the radiation detection apparatuses in the first imaging.

12. The image processing method according to claim 9, further comprising:
receiving at least one of an instruction for rearrangement of the images and an instruction for rotation of the images; and
changing at least one of the relative position and the angle stored in the storage unit in response to the instruction.

13. The image processing method according to claim 9, further comprising:
receiving a relative position and an angle of each of the radiation detection apparatuses; and
storing the received relative position and the received angle in the storage unit.

14. The image processing method according to claim 9, wherein, in a case where a disposition direction of the long-length platform is a supine/prone position, the angle stored in the storage unit is referred to in the combining.

15. A non-transitory storage medium recording a program for causing a computer to execute a combining operation of combining, on the basis of a relative position and an angle of each of radiation detection apparatuses attached to a long-length platform in first imaging which are stored in a storage unit, a plurality of images obtained by the radiation detection apparatuses.

16. The non-transitory storage medium according to claim 15, further comprising a determining operation of determining whether the relative position and angle of each of the radiation detection apparatuses in first imaging and a relative position and an angle of corresponding one of radiation detection apparatuses in second imaging match each other,
wherein, on the basis of a determination result in the determining operation, a plurality of images obtained by the radiation detection apparatuses in the second imaging are combined in the combining operation.

17. The non-transitory storage medium according to claim 15,
wherein the storage unit stores identification information of each of the radiation detection apparatuses in the first imaging along with the relative position and the angle, and
wherein, in a case where identification information of each radiation detection apparatus used in the second imaging and the corresponding identification information stored in the storage unit match each other, a plurality of images are combined in the combining operation on the basis of the relative position and angle of each of the radiation detection apparatuses in the first imaging.

18. The non-transitory storage medium according to claim 15, further comprising:
a first accepting operation of receiving at least one of an instruction for rearrangement of the images and an instruction for rotation of the images; and
a managing operation of changing at least one of the relative position and the angle stored in the storage unit in response to the instruction.

19. The non-transitory storage medium according to claim 15, further comprising:
a second accepting operation of receiving a relative position and an angle of each of the radiation detection apparatuses; and
a managing operation of storing the relative position and the angle received in the second accepting operation in the storage unit.

20. The non-transitory storage medium according to claim 15, wherein, in a case where a disposition direction of the long-length platform is a supine/prone position, the angle stored in the storage unit is referred to in the combining operation.

* * * * *